United States Patent [19]
Creed et al.

[11] Patent Number: 6,050,938
[45] Date of Patent: *Apr. 18, 2000

[54] PORTABLE ENDOSCOPY SYSTEM

[75] Inventors: Judith Creed, Merion; Joseph Spiegel, Bala Cynwyd; Peter Lambert, Paoli, all of Pa.

[73] Assignee: Swellow Vision, Inc., Merion, Pa.

[*] Notice: This patent issued on a continued prosecution application filed under 37 CFR 1.53(d), and is subject to the twenty year patent term provisions of 35 U.S.C. 154(a)(2).

[21] Appl. No.: 08/954,839

[22] Filed: Oct. 21, 1997

[51] Int. Cl.$^7$ ........................................ A61B 1/00
[52] U.S. Cl. ........................................ 600/101; 600/103
[58] Field of Search ........................ 600/101, 102, 600/103, 160, 126, 169; 434/429, 262, 263, 267; 433/77, 128

[56] References Cited

U.S. PATENT DOCUMENTS

| | | | |
|---|---|---|---|
| 4,590,923 | 5/1986 | Watanabe | 600/102 |
| 4,601,284 | 7/1986 | Arakawa et al. | 600/102 |
| 4,854,301 | 8/1989 | Nakajima | 600/102 |
| 4,998,282 | 3/1991 | Shishido et al. | 600/102 |
| 5,127,394 | 7/1992 | Lane | 600/101 |
| 5,184,601 | 2/1993 | Putman | 600/102 |
| 5,331,949 | 7/1994 | Funakoshi et al. | 600/160 |
| 5,509,810 | 4/1996 | Schertz | 434/262 |
| 5,701,903 | 12/1997 | Sano et al. | 600/160 |

FOREIGN PATENT DOCUMENTS

| | | | |
|---|---|---|---|
| 6245895 | 9/1994 | Japan | 600/102 |

OTHER PUBLICATIONS

Publication of NASA, "Technical Support Package: Compact Instrumentation Package for Remote Medical Diagnosis" NASA Tech Briefs MSC–22624, (date unknown), Lyndon B. Johnson Space Center, National Aeronautics and Space Administration (19 pages).

Primary Examiner—Paul J. Hirsch
Attorney, Agent, or Firm—Akin, Gump, Strauss, Hauer & Feld, L.L.P.

[57] ABSTRACT

A portable endoscopy system for performing an endoscopic procedure is stored in a single portable housing, where the housing and system are transportable by hand to a patient. The housing has an endoscope housing compartment, a video housing compartment, and a power supply housing compartment. The endoscope housing compartment stores a light source and a video camera. The light source provides light to an endoscope which is inserted within the patient to a predetermined area. The endoscope directs the provided light to the predetermined area and provides a light image thereof. The video camera receives the provided light image, and provides an electronic image thereof. The video housing compartment stores a video recording and playback device and a video monitor. The video recording and playback device receives and records the provided electronic image during a record mode, and provides the recorded image during a playback mode. The video monitor receives and displays the provided electronic image during the record mode, and receives and displays the provided recorded image during the playback mode. The power supply housing compartment stores a power supply supplying power to the system.

16 Claims, 3 Drawing Sheets

PORTABLE ENDOSCOPY SYSTEM

CROSS-REFERENCE TO RELATED APPLICATIONS

Not Applicable.

FIELD OF THE INVENTION

The present invention relates to a portable video endoscopy system, and more particularly to such a system with particular applicability for studying and evaluating swallowing dysfunction in a patient.

BACKGROUND OF THE INVENTION

Video endoscopy is known and widely used by medical professionals.

A video endoscopy system typically includes a light source, a fiber-optic endoscope, a video camera, a television monitor, and a VCR for recording video signals. However, such a typical video endoscope system is not intended to be mobile, and is therefore not readily movable from location to location. Instead, a patient must be brought to the system. In the rare case where a video endoscope system having the aforementioned elements is at least minimally mobile, the system is relatively heavy (over 100 pounds), and must be laboriously packed into and unpacked from multiple transportation containers, or at the very least relocated on a large rolling cart.

In nursing homes and other long-term care facilities, one of the leading causes of death is aspiration of salivary secretions, food, and/or liquid due to swallowing dysfunction, and pneumonia resulting therefrom. Moreover, such aspiration an/or pneumonia is one of the most common diagnoses leading to the need for extended hospitalization and further medical intervention in this patient population. Aside from such aspiration, swallowing dysfunction often manifests itself in nursing home residents as malnutrition. In particular, swallowing dysfunction often causes many nursing home residents to lose the motivation and physical ability to consume enough liquid and solid oral nutrition to sustain themselves. As a result, if indicated, a patient in a nursing home may require a swallowing assessment to determine risk of aspiration, to determine the ability to maintain an adequate oral diet, and to make other critical nutritional decisions.

Swallowing assessment often requires a direct examination of the pharyngeal stage of swallowing. Video endoscopy is a preferred method for performing such direct examination. However, because such video endoscopy for a long-term patient has heretofore required either: (1) patient transport from a long-term care setting to a hospital or other facility or (2) transportation of unwieldy video endoscopy equipment to the patient's setting, the availability of the endoscopy has been limited. As a result, it has been difficult to formulate a program to manage swallowing function in long-term care settings based upon endoscopic evaluation. Accordingly, a need exists for an efficient system and method for performing swallowing assessment at a bedside of a patient in a long-term care setting or the like. More specifically, a need exists for a swallowing assessment system and method that efficiently evaluates and manages swallowing disorders such that the incidence of aspiration and malnutrition can be reduced, thereby also reducing mortality, morbidity, and the cost of extensive medical evaluation and treatment. Moreover, a need exists for such a system and method wherein accurate, timely information can be provided to guide the patient, family and medical staff in the nutritional decisions critical to health and quality of life.

BRIEF SUMMARY OF THE INVENTION

The aforementioned needs are satisfied by the video endoscopy system and method of the present invention. In particular, in the present invention, a hand-portable endoscopy system for performing an endoscopic procedure is stored in a single hand-portable housing, and the housing and system are transportable by hand to a patient. The housing has an endoscope housing compartment, a video housing compartment, and a power supply housing compartment.

The endoscope housing compartment stores a light source and a video camera. The light source provides light to an endoscope coupled thereto, where the endoscope is inserted within the patient to a predetermined area, directs the provided light from the light source to the predetermined area within the patient, and provides a light image of the predetermined area. The video camera is coupled to the endoscope, receives the provided light image, and provides the received light image as an electronic image.

The video housing compartment stores a video recording and playback device and a video monitor. The video recording and playback device is coupled to the video camera to receive and record the provided electronic image during a record mode, and provides the recorded image during a playback mode. The video monitor is coupled to the video camera and to the video recording and playback device. The video monitor receives and displays the provided electronic image from the video camera during the record mode, and also receives and displays the provided recorded image from the video recording and playback device during the playback mode. The power supply housing compartment stores a power supply for supplying power to the system. The system and housing are capable of being hand carried by a person from one location to another without benefit of auxiliary transportation means.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
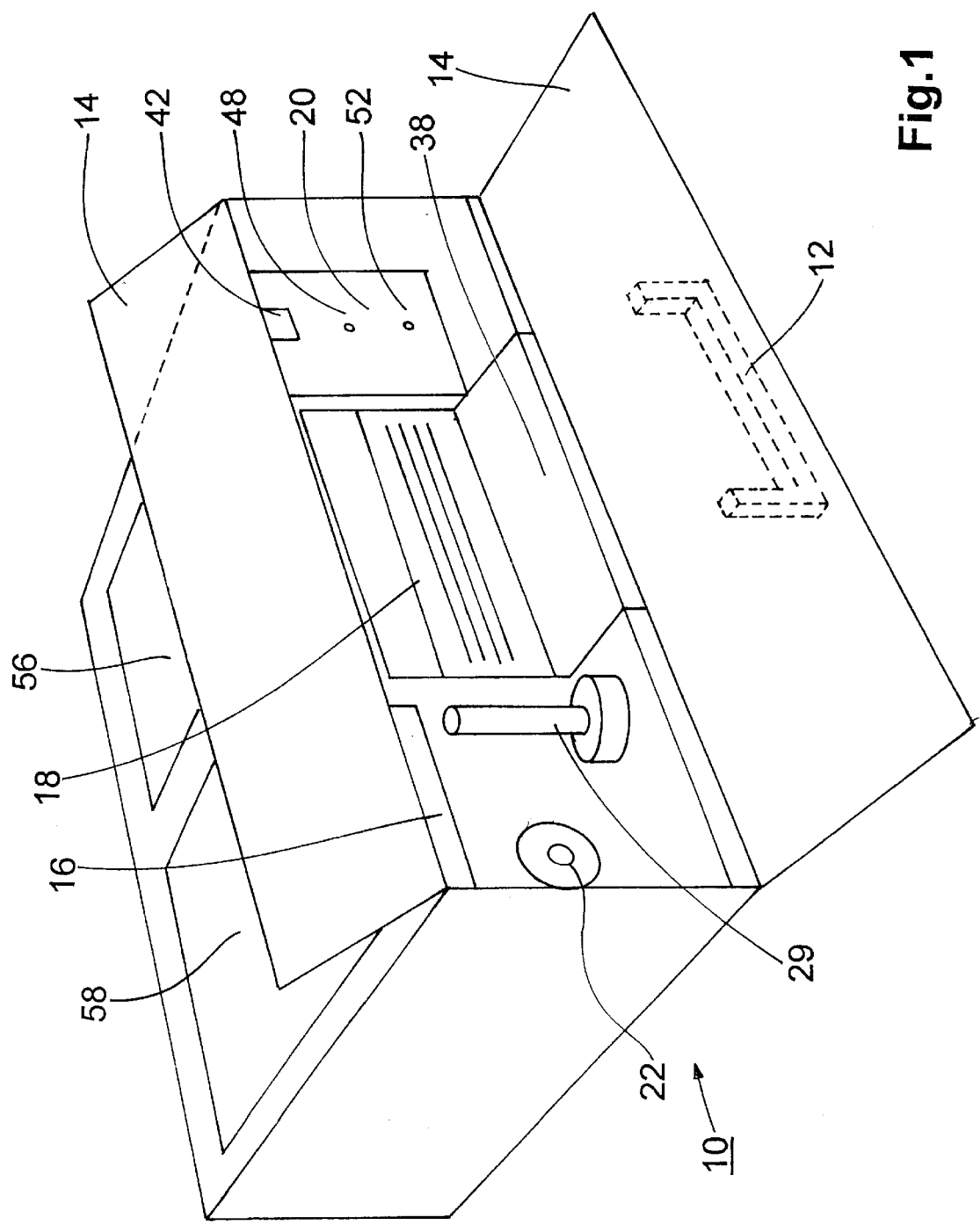
FIG. 1 is a perspective view of a hand-portable endoscopy system in a single hand-portable housing in accordance with a preferred embodiment of the present invention, where the system is stored within the closed housing.

Certain terminology may be used in the following description for convenience only and is not limiting. The words "left", "right", "upper", and "lower" designate directions in the drawings to which reference is made. The words "inwardly" and "outwardly" are further directions toward and away from, respectively, the geometric center of a referenced object. The terminology includes the words above specifically mentioned, derivatives thereof, and words of similar importance.

Figure 2:
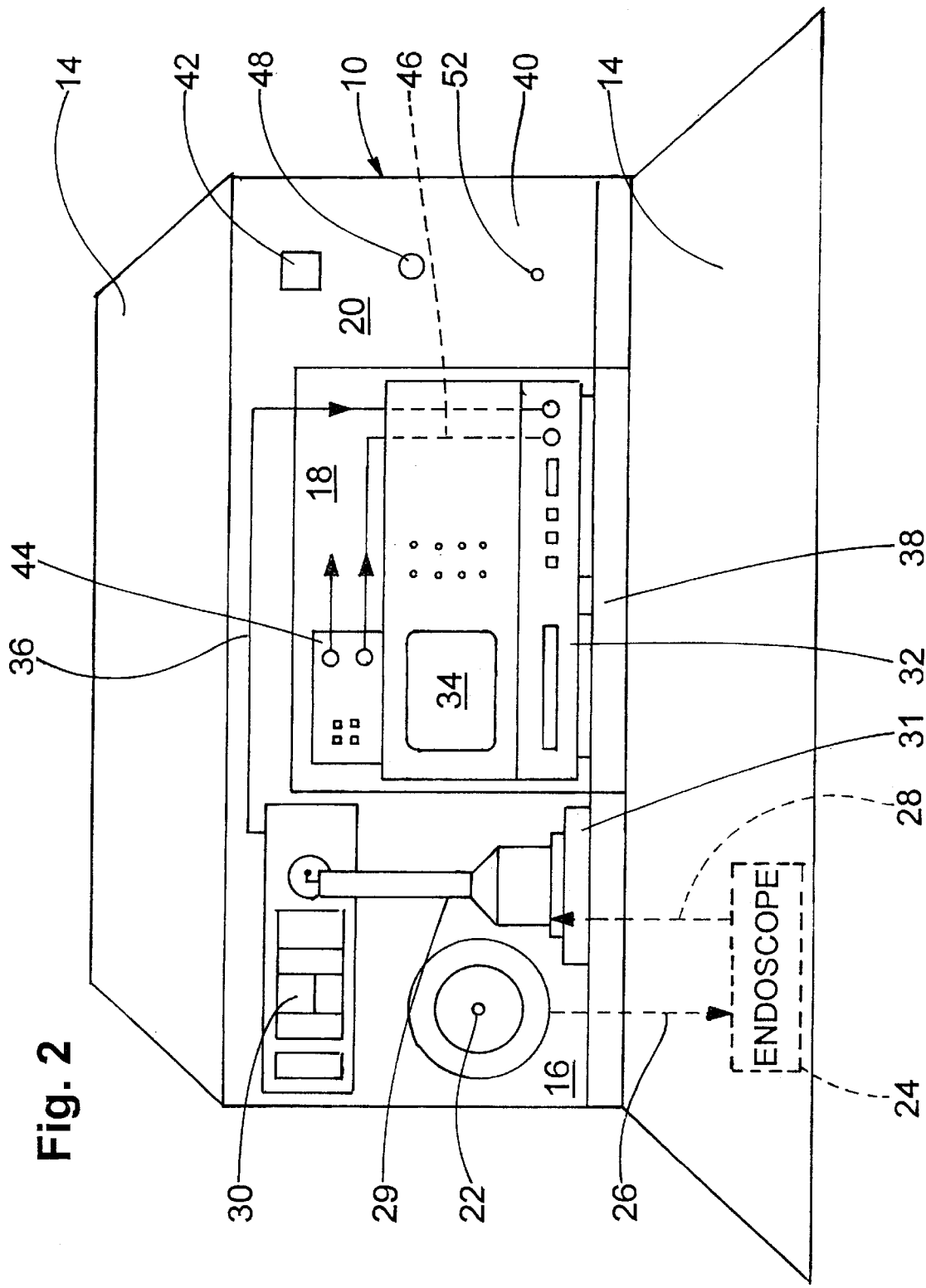
FIG. 2 is an elevational view of the system and housing of FIG. 1, where the housing is opened and the endoscopy system is available for use.

Referring to the drawings in detail, wherein like numerals are used to indicate like elements throughout, there is shown in FIGS. 1 and 2 a hand-portable endoscopy system and a single hand-portable housing 10 for storing the system in accordance with a preferred embodiment of the present invention. As seen, the housing 10 stores the endoscopy system and allows the endoscopy system to be transported by hand to a patient (not shown). Since the housing 10 and the endoscopy system are hand-portable, it is preferable that the housing 10 include one or more handles 12 to allow the housing 10 to be carried with relative ease. In addition, or in the alternative, the housing 10 may be provided with other means to enhance portability. For example, appropriate wheels (not shown) may be positioned at the base of the housing 10, the housing 10 may be placed on a rolling cart, or the housing 10 may be positionable on a hand truck or the like, among other things, all without departing from the spirit and scope of the present invention.

Once the housing 10 has been moved to and positioned at an appropriate location adjacent a patient, the housing 10 is opened to expose the endoscopy system such that an endoscopic procedure may be performed on the patient. In the preferred embodiment of the present invention, the endoscopic procedure is a direct examination in connection with a swallowing assessment of a patient. However, one skilled in the art will recognize that other types of endoscopic procedures may be performed without departing from the spirit and scope of the present invention. For example, the endoscopic procedure may be a colonoscopy, a peniloscopy, a hysteroscopy, or a bronchoscopy, among other things.

As seen in FIG. 1, the housing 10 has a pair of panels 14 that fold out to expose the interior of the housing 10. However, one skilled in the art will recognize that any of a plurality of opening devices may be employed in the housing 10 without departing from the spirit and scope of the present invention. For example, the panels 14 may instead be replaced by a single panel, by a roll-up panel, or by a detachable panel, among other things. As seen, the handle 12 is positioned on one of the panels 14.

In the preferred embodiment of the present invention, the housing 10 has three general areas or compartments: an endoscope housing compartment 16, a video housing compartment 18, and a power supply housing compartment 20. As one skilled in the art will appreciate, the configurations of the compartments 16, 18, 20, may be functionally defined according to size and other requirements, and the compartments 16, 18, 20 may be physically defined by any of several compartment-forming schemes, all without departing from the spirit and scope of the present invention. For example, each compartment 16, 18, 20, may be defined in an internal metal housing positioned within the housing 10, where each compartment 16, 18, 20 can be individually opened for access to and/or repair of individual components therein.

Referring specifically to FIG. 2 now, the endoscope housing compartment 16 has a light source 22 that is to be coupled to an endoscope 24 by way of an appropriate coupling on the light source 22. Preferably, the endoscope 24 is a fiber-optic endoscope and includes a first fiber-optic light guide 26 that is attached at a distal end thereof to the light source 22, although one skilled in the art will appreciate that other types of endoscopes and light guides may be employed without departing from the spirit and scope of the present invention. In FIG. 2, the endoscope 24 is shown in phantom for the reason that the endoscope 24 is not necessarily stored within the housing 10. In particular, since the endoscope is to be inserted within the patient and must therefore be sterilized, the endoscope 24 most likely will be removed from a sterilizing system (not shown) and coupled to the light source 22 by way of the first light guide 26 just prior to the endoscopic procedure. As should be understood, then, the endoscope 24 may be stored separate from the housing 10 or inside the housing 10. The light source 22 and the endoscope 24 may each be any of several known light sources and endoscopes, respectively, without departing from the spirit and scope of the present invention. However, the light source 22 should be comparatively small so as to fit within the endoscope housing compartment 16 of the housing 10, and the endoscope 24 should likewise be comparatively small if it is to fit within the endoscope housing compartment 16 of the housing 10. In one preferred embodiment of the present invention, the light source 22 is a WELCH-ALLYN light source, model no. REF49501. In the case of a video endoscopic swallowing assessment or study, the endoscope 24 is preferably a flexible nasopharyngoscope. In one preferred embodiment of the present invention, such endoscope 24 is an OLYMPUS ENF type P3 nasopharyngoscope or a comparable product.

Upon inserting the endoscope 24 within the patient, a proximal end of the endoscope 24 is maneuvered to a predetermined area. The first light guide 26 of the endoscope 24 channels light provided from the light source 22 to the proximal end of the endoscope 24 and then to the predetermined area within the patient. The endoscope 24 also includes a light collecting device at the proximal end that is positioned toward the predetermined area, and a second fiber-optic light guide 28 that directs a light image of the predetermined area from the light collecting device up through and out of the endoscope 24 to a viewing device. Preferably, each of the first and second light guides 26, 28 of the endoscope 24 comprises a fiber-optic bundle that is external and internal to the endoscope 24 and that extends within the endoscope 24 to the proximal end thereof.

As seen in FIG. 2, the second light guide 28 of the endoscope 24 is operatively coupled to a video camera 30 within the endoscope housing compartment 16 and transmits the light image thereto. More specifically, the viewing device of the second light guide 28 is operatively coupled to a camera lens 29 attached to the video camera 30 which focuses the transmitted light image and forwards the focused light image to the video camera 30. The video camera 30 receives the light image provided by the endoscope 24 by way of the lens 29, and converts the received light image into an electronic image in a well known manner. The video camera 30 may be any of several known video cameras without departing from the spirit and scope of the present invention. However, the video camera 30 should be comparatively small so as to fit within the endoscope housing compartment 16 of the housing 10. In one preferred embodiment of the present invention, such video camera 30 is a PANASONIC video camera, model no. GP-KS152. Preferably, the lens 29 of the video camera 30 is stored within the endoscope housing compartment 16 in a storage coupling 31 when not coupled to the endoscope 24.

Within the video housing compartment 18 of the housing 10 is stored a video recording and playback device 32 and a video monitor 34. As seen in FIG. 2, the video recording and playback device 32 is coupled to the video camera 30 by an appropriate cable 36 such that the video recording and playback device 32 can be selectively operated to receive and record an electronic image provided by the video camera 30 during a record mode. In addition, the video recording and playback device 32 can also be selectively operated to provide the recorded image during a playback mode.

The video monitor 34 is coupled to the video camera 30 and also to the video recording and playback device 32. Accordingly, during the record mode, the video monitor 34 receives and displays the provided electronic image from the video camera 30. Likewise, during the playback mode, the video monitor 34 receives and displays the provided recorded image from the video recording and playback device 32.

As should now be understood, during the performance of the video endoscopic swallowing study or any other endoscopic study or examination with the system and housing 10 of the present invention, a clinician will typically employ the video monitor 34 as a viewing device during insertion of the endoscope 24 and during the exploration of the patient therewith. Moreover, during such study, the clinician will typically employ the video recording and playback device 32 to make a video record of the study, and a physician or other specialist may then at a later time employ the video record of the study from the video recording and playback device 32 to make a functional diagnosis.

The video recording and playback device 32 and the video monitor 34 may comprise separate physical structures, although in the preferred embodiment of the present invention, the video recording and playback device 32 and the video monitor 34 are a combined video recording, playback and display device, as shown in FIG. 2. Accordingly, no external connecting cable between the video recording and playback device 32 and the video monitor 34 is shown in FIG. 2. The video recording and playback device 32 and the video monitor 34, whether combined or separate, may be any of several well known video recording and playback devices and video monitors without departing from the spirit and scope of the present invention. However, the video recording and playback device 32 and the video monitor 34 must be comparatively small in order that they may be positioned within the video housing compartment 18 of the housing 10. In one preferred embodiment of the present invention, such video recording and playback device 32 and such video monitor 34 are a SONY combined TV/VCR, model no. GV-550 NTSC, where the VCR is a Hi-8 format VCR.

Preferably, at least the video monitor 34 is positioned on a retractable shelf 38. Accordingly, a clinician employing the system and housing 10 can pull out the shelf 38 for more accessible viewing of the video monitor 34. More preferably, the retractable shelf 38 is a swiveling shelf for improved accessability and visibility. As seen in FIGS. 1 and 2, at least the video monitor 34 may pivot forward on the shelf 38 from a storage position to a viewing position.

A power supply 40 is stored within the power supply housing compartment 20 of the housing 10. The power supply 40 supplies power to the entire endoscope system, including the light source 22, the video camera 30, the video recording and playback device 32, and the video monitor 34. Preferably, the power supply 40 includes an on/off switch 42, and each element in the endoscope system is powered to a ready state and the system is ready for operation when the switch 42 is moved from an off position to an on position.

The power supply 40 may be any of several well known power supplies without departing from the spirit and scope of the present invention. However, the power supply 40 must be relatively small to fit within the power supply housing compartment 20. If the power requirements of the system within the housing 10 are not unusual, the power supply 40 may merely comprise a switched power strip, wherein each element may draw power by being plugged into the strip, and the strip may in turn be plugged into an available power outlet. However, if the power requirements of the elements are unusual or exacting, the power supply 40 may be a more sophisticated power conditioning and supplying device with an input from an available power outlet and specific outputs for each element. In either case, it is preferable that the available power outlet be a standard power outlet such that portability of the system and housing 10 is enhanced.

Figure 3:
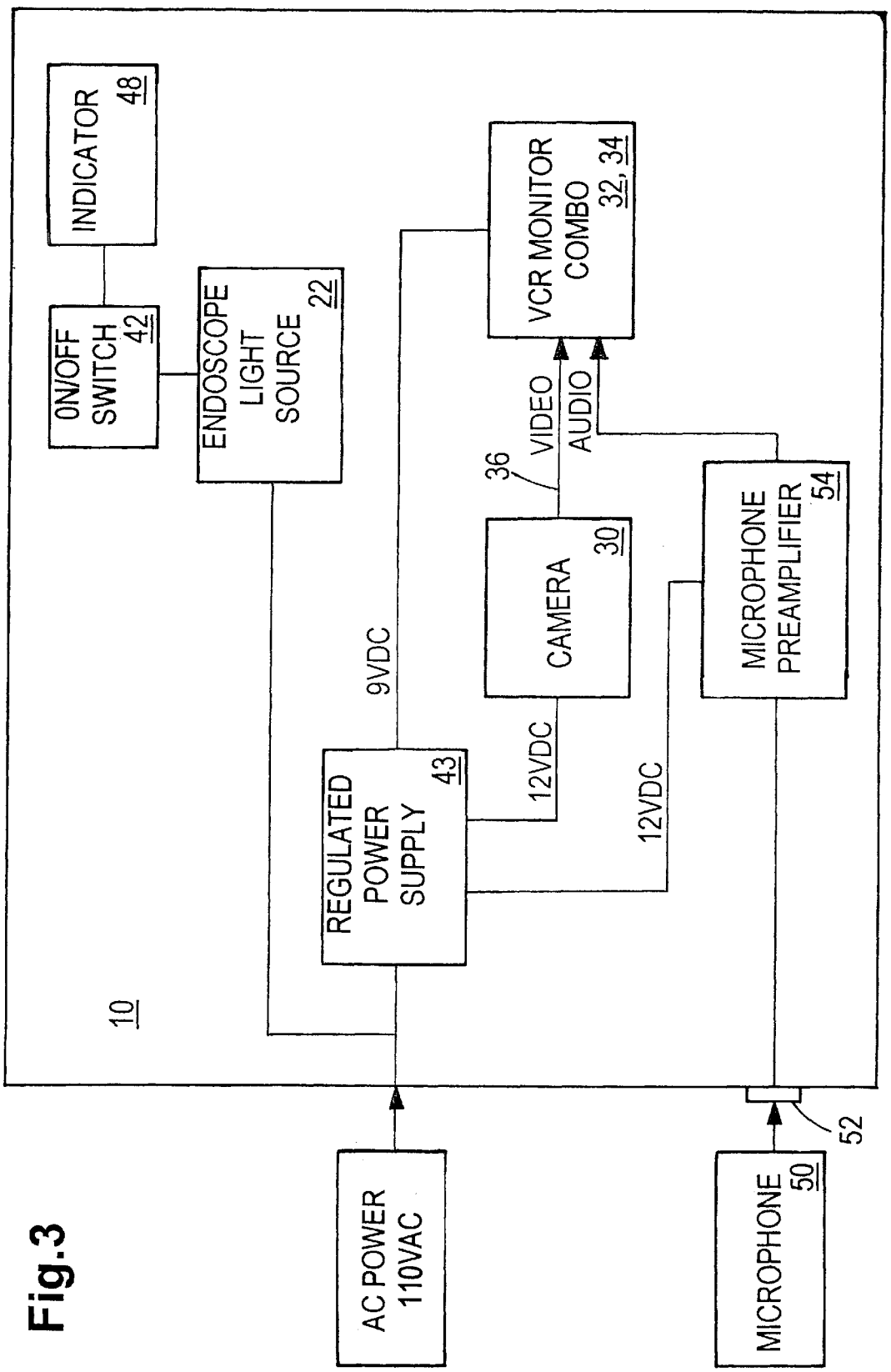
FIG. 3 is a schematic diagram illustrating the electrical connections of several of the components of the system of FIGS. 1 and 2.

In a preferred embodiment of the present invention, and referring now to FIG. 3, the power supply 40 includes a regulated power supply 43 that receives input power from a standard 110 VAC power outlet and that supplies low voltage DC power to the video camera 30 and the video recording and playback device 32 and the video monitor 34. Here, the on/off switch 42 controls the light source 22, and an indicator 48 (FIG. 2) lights to show when power is being supplied by such switch 42.

Preferably, a microphone 50 may be supplied with the system and housing 10 such that recorded endoscopic images may be supplemented with audio details. As seen in FIGS. 2 and 3, the microphone is preferably plugged into an appropriate microphone jack 52 on the housing 10, the jack 52 leads to an appropriate pre-amplifier 54, and the pre-amplifier 54 leads to the video recording and playback device 32 and the video monitor 34. Preferably, the power supply 40 supplies low voltage DC power to the pre-amplifier 54.

Preferably, and referring now to FIG. 1, the housing 10 includes a power cord storage pouch on an exterior surface thereof such that a power cord (not shown) for the power supply 40 may be conveniently stored therein. The housing 10 may additionally include an auxiliary pouch 58 for storing other materials, i.e., notepads, recording media, a pre-sterilized endoscope 24, etc.

In the case of a video endoscopic swallowing assessment or study, where the endoscope 24 is a flexible nasopharyngoscope, the study is preferably performed on a patient with the system and housing 10 of the preferred embodiment of the present invention in the following manner:

Preliminarily, and as is to be expected, the system and housing must be transported to an appropriate location adjacent the patient and then set up. Typically, such set up includes: opening the panels 14 or the like to expose the system in the housing 10; connecting the power supply 40 in the power supply housing compartment 20 to an available outlet; removing the endoscope 24 from a sterilizing system; coupling the first light guide 26 of the endoscope 24 to the light source 22 within the endoscope housing compartment 16; coupling the second light guide 28 of the endoscope 24 to the video camera 30 within the endoscope housing compartment 16; and powering on the system by moving the switch 42 on the power supply 40 from the off position to the on position. Thereafter, if a video record of the study is desired for later use, an appropriate recording medium is placed into the video recording and playback device 32 and such video recording and playback device 32 is operated in the record mode. The study may then proceed.

The endoscope 24 is first passed through the nose of a patient. If the patient's nose is particularly obstructed, a vasoconstrictor agent such as oxymetazoline hydrochloride may be employed, and if the patient is very uncomfortable, a topical anesthetic such as pontocaine spray can be applied. However, the use of nasal anesthetic should be limited so that the sensation in the tongue base, pharynx, and larynx are not diminished during the study.

When first entering the nose, it is important to examine the anatomy of the nasal cavity to detect any obstruction which might alter the ability of the endoscope 24 to be passed comfortably. Usually, one side of the nose is more amenable to the study than the other because of deviations in the nasal septum. In very rare cases, the nose is completely obstructed due to polyps or septal deformity and the study must be aborted. Assuming the endoscope 24 can be passed through to the back of the nose, the endoscope 24 is then advanced into the oropharynx.

When the vocal folds are visualized, the examiner should initially evaluate anatomy and function of the tongue, palate, pharynx and larynx. Any abnormal lesion, asymmetry, paresis or paralysis should be noted and considered in relation to swallowing ability. Laryngeal motion and the integrity of glottic closure are documented. At some point, laryngeal sensation and cough reflex are evaluated by touching the arytenoid cartilage surfaces with the tip of the endoscope 24, or using other methods such as endoscopic air pulse stimulation. Preferably, the examiner waits until all swallowing trials are completed before attempting to test sensation palpably. If the patient gags early in the study, the gag reflex can be heightened throughout the study and thereby alter such study.

Before swallowing trials begin, the examiners should observe the level of secretions in the pharynx. An accurate assessment of the patient's ability to manage their own secretions is a primary determinant of swallowing function and can help the examiner to plan appropriate swallowing trials.

Next, the swallowing trials can take place. In such swallowing trials, the endoscope 24 is held just below the level of the soft palate while the patient is asked to swallow multiple boluses of dyed food of varied consistencies. Soft foods such as applesauce and pudding are used, followed by liquid of varied consistencies. The dye is preferably a simple food dye. Multiple swallows are assessed to determine the effects of variation in bolus size or consistency, head position and compensatory swallowing maneuvers. If the patient is reclined prior to the study, it may be necessary to right them. Often the patient will tend to lean to a side. In this case, they should be encouraged to sit upright during the study. However, the examiner should try to mimic the patient's position during routine feedings.

While the patient is swallowing, the examiner operating the endoscope 24 should attempt to follow the bolus as it progresses through the pharynx. If the endoscope 24 is too close to the larynx during the swallow, the endoscope 24 may actually touch the epiglottis when the larynx elevates during the pharyngeal stage of swallowing. If, however, the endoscope 24 is too far away from the larynx after the swallow, it will be difficult to observe retention and laryngeal penetration. During the oral stage of swallowing, the examiner should hold the endoscope 24 just below the level of the soft palate. There is always a brief white-out in the endoscopic image when the pharynx maximally contracts. Immediately after the white-out of the pharyngeal stage swallow, the examiner advances the endoscope 24 above the epiglottis to observe retained materials in the vallecula, and then, if possible, advances further to observe any retention in the pyriform sinuses or post cricoid space, or to observe if there has been any laryngeal penetration. If aspiration is suspected or observed, the examiner should maintain the position of the endoscope 24 above the vocal folds and ask the patient to cough. If the initial cough produces dyed materials, then aspiration is confirmed. If the patient aspirates some material, but spontaneously clears it with an un-cued, strong cough, then this may influence the determination of risk to develop aspiration pneumonia.

When swallowing trials are complete, the examiner operating the endoscope 24 can test sensation by stimulating the arytenoid cartilage surfaces, the aryepiglottic folds, or vocal folds. The functional source of dysphagia may be a lack of oral control of the bolus causing premature spillage into the pharynx or larynx, a lack of strength or coordination in the pharyngeal or esophageal mechanisms, a mechanical obstruction, or a loss of airway protection (decreased sensation and poor respiratory status). The highest risk of aspiration occurs in patients with a combination of muscular and sensory deficits.

Finally, the endoscope 24 is withdrawn from the patient, as the study is complete. If a video record of the study is being made, the video recording and playback device 32 is stopped, and such video recording and playback device 32 may be operated in the playback mode to immediately replay the study. Alternatively, the video recording and playback device 32 may be operated in the playback mode at a later time to replay the study and/or the recording medium may be removed from the video recording and playback device 32 and the study may be replayed at a later time on another video recording and playback device.

After the study is complete, the system and housing 10 are typically packed up for transportation to another location. Such pack up includes: powering off the system by moving the switch 42 on the power supply 40 from the on position to the off position; decoupling the endoscope 24 from the light source 22 and from the video camera 30; disconnecting the power supply 40 from the outlet; and closing the panels 14 or the like on the housing 10. Of course, one skilled in the art will recognize that many different types of studies can be performed with the system and housing 10 of the preferred embodiment of the present invention, and that many different particular steps can be performed before, during, and after any such study, all without departing from the spirit and scope of the present invention.

In certain instances, it may be useful to be able to transmit electronic images from the video camera 30 and/or recorded images from the video recording and playback device 32 to a remote location. Accordingly, such transmitted images may either be remotely viewed immediately or remotely recorded for later playback. If such functionality is desired, it is preferable that the system and housing 10 include a video transmitter 44 coupled to the video camera 30 and to the video recording and playback device 32 by way of an appropriate cable 46. As seen in FIG. 2, the cable 46 extends between the video transmitter 44 and the video recording and playback device 32 only. However, it is to be understood that the video transmitter 44 also has access to the video camera 30 by way of the cable 36 connecting the video recording and playback device 32 and the video camera 30.

The video transmitter 44 may be any of several known video transmitters without departing from the spirit and scope of the present invention. However, the video transmitter 44 must be comparatively small to fit within the housing 10. As seen in FIG. 2, the video transmitter 44 is positioned within the video housing compartment 18 of the housing 10.

Preferably, the housing 10 is large enough to accommodate all of the elements that are to be positioned and stored therein for transportation to and from a patient. However, and as should be understood, the housing 10 must be small enough so as to be portable with relative ease. Preferably, the housing 10 with the endoscope system stored therein has a total weight less than about 50 pounds. More preferably, the housing 10 with the endoscope system stored therein house a total weight less than about 25 pounds. Also preferably, the housing 10 when viewed as in FIG. 2 is about 18 inches wide, about 7 inches tall, and about 13 inches deep. Accordingly, the system and housing 10 may be moved with relative ease within a long-term care facility or the like, and may also be moved with relative ease between a vehicle and a nearby building, for example.

From the foregoing description, it can be seen that the present invention comprises a new and useful system and housing and method for performing endoscope studies including video endoscopic swallowing studies. The system may be placed at and the study may be performed at a bedside of a patient in a long-term care setting or the like for efficiently evaluating and managing swallowing disorders such that the incidence of aspiration and malnutrition can be reduced, thereby also reducing mortality, morbidity, and the cost of extensive medical evaluation and treatment. It will be appreciated by those skilled in the art that changes can be made to the embodiments described above without departing from the broad inventive concepts thereof. It is understood, therefore, that this invention is not limited to the particular embodiments disclosed but is intended to cover modifications within the spirit and scope of the present invention as defined by the appended claims.

We claim:

1. A hand-portable endoscopy system and a single hand-portable housing for storing the system and for readily transporting the system by hand to a patient regardless of where that patient may be located, the system for performing a medical endoscopic procedure including evaluation of swallowing dysfunction, a colonoscopy, a peniloscopy, a hysteroscopy or a bronchoscopy, the system and housing comprising at least:

an endoscope housing compartment within which is stored:
 a light source for providing light to an endoscope coupled thereto, the endoscope for being inserted within the patient to a predetermined area for directing the provided light from the light source to the predetermined area within the patient, and for providing a light image of the predetermined area; and
 a video camera for being functionally coupled to the endoscope, the video camera for receiving the provided light image and for providing the received light image as an electronic image;

a video housing compartment within which is stored:
 a video recording and playback device functionally coupled to the video camera, the video recording and playback device for receiving and recording the provided electronic image during a record mode and for providing the recorded image during a playback mode; and
 a video monitor coupled to the video camera and to the video recording and playback device, the video monitor for receiving and displaying the provided electronic image from the video camera during the record mode, the video monitor also for receiving and displaying the provided recorded image from the video recording and playback device during the playback mode; and a power supply housing compartment within which is stored a power supply for supplying power to the system, said light source, video camera, video recording and playback device, video monitor and power supply being functionally integrated within said housing, said system and housing having a total weight less than about 50 pounds;

wherein said system and housing are capable of being transported by hand from one location to another by a person without benefit of auxiliary transportation means.

2. The system and housing of claim 1 wherein the power supply includes an on/off switch, and wherein the light source, the video camera, the video recording and playback device, and the video monitor are powered to a ready state and the system is ready for operation when the switch is moved from an off position to an on position.

3. The system and housing of claim 1 wherein the video recording and playback device and the video monitor comprise a combined video recording, playback, and display device.

4. The system and housing of claim 3 wherein the video housing compartment includes a retractable shelf on which the video recording, playback, and display device is stored.

5. The system and housing of claim 1 wherein the system and housing have a total weight less than about 25 pounds.

6. The system and housing of claim 1 further comprising an endoscope, wherein the endoscope is a nasopharyngoscope.

7. The system and housing of claim 1 wherein the video monitor is mounted on a retractable, swiveling shelf.

8. The system and housing of claim 1 wherein the power supply supplies power to the entire system including, the light source, video camera, video recording and playback device, and video monitor.

9. A method of storing a portable endoscopy system within a single hand-portable housing and for transporting the system by hand to a patient regardless of where that patient may be located, the system for performing a swallow evaluation endoscopic procedure using a nasopharyngoscope, the method comprising the steps of:

providing within the housing an endoscope housing compartment;

storing within the endoscope housing compartment:
 a light source for providing light to an endoscope coupled thereto, the endoscope for being inserted within the patient to a predetermined area, for directing the provided light from the light source to the predetermined area within the patient, and for providing a light image of the predetermined area; and
 a video camera coupled to the endoscope, the video camera for receiving the provided light image and for providing the received light image as an electronic image;

providing within the housing a video housing compartment;

storing within the video housing compartment:
 a video recording and playback device coupled to the video camera, the video recording and playback device for receiving and recording the provided electronic image during a record mode and for providing the recorded image during a playback mode; and a video monitor coupled to the video camera and to the video recording and playback device, the video monitor for receiving and displaying the provided electronic image from the video camera during the record mode, the video monitor also for receiving and displaying the provided recorded image from the video recording and playback device during the playback mode;

providing within the housing a power supply housing compartment;

storing within the power supply housing compartment a power supply for supplying power to the system;

said housing and system weighing less than about 50 pounds; and personally transporting the housing and the system by hand to the patient without benefit of auxiliary transportation means.

10. The method of claim 9 wherein the power supply includes an on/off switch, the method further comprising the step of moving the switch from an off position to an on position such that the light source, the video camera, the video recording and playback device, and the video monitor are powered and at a ready state, the system thereby being ready for operation.

11. The method of claim 9 wherein the storing within the video housing compartment step comprises storing a combined video recording, playback, and display device.

12. The method of claim 11 further comprising the step of providing within the video housing compartment a retractable shelf on which the video recording, playback, and display device is stored.

13. The method of claim 9 further comprising the step of having the system and housing weight less than about 25 pounds.

14. T he method of claim 9 wherein the hand portable endoscopy system is selected from the group consisting of colonoscope, peniloscope, hysteroscope, bronchoscope and nasopharyngoscope.

15. A hand-portable endoscopy system and a single hand-portable housing for storing the system and for readily transporting the system by hand to a patient regardless of where that patient may be located, the system for performing an endoscopic swallow evaluation procedure, the system and housing comprising:

an endoscope housing compartment within which is stored at least:
   a light source for providing light to an endoscope coupled thereto, the endoscope for being inserted within the patient to a predetermined area, for directing the provided light from the light source to the predetermined area within the patient, and for providing a light image of the predetermined area; and
   a video camera for being coupled to the endoscope, the video camera for receiving the provided light image and for providing the received light image as an electronic image;

a video housing compartment within which is stored:
   a video recording and playback device coupled to the video camera, the video recording and playback device for receiving and recording the provided electronic image during a record mode and for providing the recorded image during a playback mode; and
   a video monitor coupled to the video camera and to the video recording and playback device, the video monitor for receiving and displaying the provided electronic image from the video camera during the record mode, the video monitor also for receiving and displaying the provided recorded image from the video recording and playback device during the playback mode; and a power supply housing compartment within which is stored a power supply for supplying power to the system, said system and housing having, a total weight less than about 50 pounds, said light source, video camera, video recording and playback device, video monitor and power supply being functionally integrated within said housing, wherein the system and housing are capable of being hand carried from one location to another by a person without benefit of auxiliary transportation means.

16. The system and housing of claim 15 wherein the system and housing have a total weight less than about 25 pounds.

* * * * *